(12) United States Patent
Kulper et al.

(10) Patent No.: US 10,966,842 B2
(45) Date of Patent: Apr. 6, 2021

(54) SURGICAL EXTRACTION DEVICE FOR BONE IMPLANT TIPS

(71) Applicant: THE UNIVERSITY OF HONG KONG, Hong Kong (CN)

(72) Inventors: Sloan Austin Kulper, Hong Kong (CN); Erica Ann Boles, Hong Kong (CN); Xinshuo Christian Fang, Hong Kong (CN); Ka Li Frankie Leung, Hong Kong (CN); Weijia William Lu, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 176 days.

(21) Appl. No.: 16/032,509

(22) Filed: Jul. 11, 2018

(65) Prior Publication Data

US 2019/0015220 A1    Jan. 17, 2019

Related U.S. Application Data

(60) Provisional application No. 62/532,220, filed on Jul. 13, 2017.

(51) Int. Cl.
*A61F 2/46* (2006.01)
*A61B 17/88* (2006.01)
(Continued)

(52) U.S. Cl.
CPC ........ *A61F 2/4603* (2013.01); *A61B 17/8847* (2013.01); *A61B 17/92* (2013.01);
(Continued)

(58) Field of Classification Search
CPC .......... A61F 2/46; A61F 2/4603; A61B 17/88; A61B 17/8847
See application file for complete search history.

(56) References Cited

U.S. PATENT DOCUMENTS

| 5,045,054 A | 9/1991 | Hood et al. |
| 5,674,225 A | 10/1997 | Müller |

(Continued)

OTHER PUBLICATIONS

Kulper, S.A. et al., Anti-Penetration Bone Implant Device and Method, U.S. Appl. No. 62/142,207, filed Apr. 2, 2015.

*Primary Examiner* — Christopher J Beccia
(74) *Attorney, Agent, or Firm* — Saliwanchik, Lloyd & Eisenschenk

(57) ABSTRACT

Devices and methods for the removal of bone implant tips from within a bony structure in a body. The device or method includes a shaft with an internal grasping feature capable of being inserted while remaining in an un-expanded, un-deployed state. This permits a surgeon or operator to insert the device while in a small profile state, avoiding or reducing damage to adjacent bone tissue during insertion. Upon insertion of the shaft to the proper position within a patient's bone, the grasping feature may then be expanded or deployed from the distal end of the shaft by a surgeon or operator using an actuator in a handle attached to the proximal end of the shaft. Following deployment, the grasping feature may be used to manipulate and/or remove a bone implant tip from a patient's bone tissue. Embodiments of the grasping feature include one or more hooks, wires, articulating fingers, and/or net-based designs formed of metal, polymer, composite, or a combination thereof. The grasping feature may also include an adhesive-based design formed of bone cement, protein-based glue, or other adhesive material with the purpose of grasping or manipulating a bone implant tip within bone tissue.

18 Claims, 6 Drawing Sheets

(51) Int. Cl.
*A61B 17/92* (2006.01)
*A61B 17/00* (2006.01)

(52) U.S. Cl.
CPC ............... *A61B 2017/00004* (2013.01); *A61F 2002/4619* (2013.01)

(56) References Cited

U.S. PATENT DOCUMENTS

| | | | |
|---|---|---|---|
| 5,782,830 A * | 7/1998 | Farris | A61L 31/024 606/99 |
| 6,312,258 B1 | 11/2001 | Ashman | |
| 6,478,801 B1 * | 11/2002 | Ralph | A61F 2/442 606/104 |
| 8,454,621 B2 * | 6/2013 | DeRidder | A61F 2/4611 606/99 |
| 2009/0317771 A1 | 12/2009 | Anitua Aldecoa | |
| 2009/0326543 A1 * | 12/2009 | Fabian, Jr. | A61F 2/4611 606/99 |
| 2011/0172673 A1 | 7/2011 | Anitua Aldecoa | |
| 2012/0004664 A1 | 1/2012 | Paul | |
| 2013/0261626 A1 | 10/2013 | Chavarria et al. | |

* cited by examiner

SURGICAL EXTRACTION DEVICE FOR BONE IMPLANT TIPS

CROSS-REFERENCE TO RELATED APPLICATION

This application claims the benefit of U.S. Provisional Application Ser. No. 62/532,220, filed Jul. 13, 2017, the disclosure of which is hereby incorporated by reference in its entirety, including all figures, tables and drawings.

BACKGROUND OF INVENTION

An increasing proportion of individuals worldwide experience fragility fractures due to osteoporosis, in which bone loses both density and structural strength. This is especially true of fractures of the hip, shoulder and spine due to their relatively high content of cancellous, or "spongy," bone tissue, which is particularly susceptible to osteoporosis.

In response to this growing clinical need, numerous devices and improvements pertaining to bone implants have been developed to improve stability and healing in osteoporotic bone following surgical repair of fractures. These devices and improvements can include the use of special bone implant tips, some of which are separable from the main implant. Bone implant tips can be rigid or pliable appliances inserted into a pilot hole in a bone for supporting a bone implant. In the case of separation of the tip from the main implant while within bone tissue, a surgeon may require a special device to aid in extraction of the tip, beyond the typical instruments available in the operating theater. Typical surgical instruments may not have the proper dimensions, grasping strength, or degrees of mechanical freedom necessary to extract a bone implant tip from within a bone, without causing additional incidental trauma to the bone tissue. In addition, bone implant tips are produced in a variety of materials and designs, including softer materials that are not easily extracted by the usual methods and devices. Therefore, a specialized instrument for cases such as the extraction of a soft polymer tip would be of particular utility during surgery.

BRIEF SUMMARY OF THE INVENTION

The embodiments of the subject invention successfully address the above-described disadvantages associated with the previously known devices and methods, and provide certain attributes and advantages, which have not been realized by these known devices. In particular, the subject invention is embodied in devices and methods that provide novel and highly effective means for the extraction of bone implant tips from within a bone, which is beyond the capabilities of typical instruments used in orthopedic surgery.

The embodiments of the current invention pertain to improved bone implant tip extraction instruments and/or methods of extracting bone implant tips. In particular, embodiments of the subject invention provide an instrument for use in the extraction of bone implant tips that inhibits additional incidental trauma to the bone tissue of the patient.

A typical bone implant pilot hole, for receiving an implant offers limited space for navigating a surgical instrument, grasping a bone implant tip, and removing the bone implant tip, without damaging bone tissue. Damage to the bone tissue of the implant pilot hole can result in various clinically undesirable outcomes, including the destruction of tapped or threaded features in the bone tissue that facilitate the insertion and removal of the bone implant. Likewise, failure to remove a bone implant tip can be clinically undesirable. For example, the implant tip may be misaligned within the pilot hole in such a manner that the implant cannot be inserted or removed.

Embodiments of the current invention include a specialized instrument with grasping features that are enclosed, retracted, contained, or otherwise hidden within a long central tube, so that these grasping features are inhibited from cutting, scraping, or otherwise damaging adjacent tissue when inserted into the bone. Following insertion of the instrument, the surgeon can deploy the above mentioned grasping features to secure the implant tip, position it advantageously, and remove it from the bone.

The instruments of the subject invention can include a handle, with a button or other user-operated control, operably attached to an elongated tube of rigid or semi-rigid material in which a grasping feature such as a hook, wire, articulating fingers, net, adhesive portion, or other design feature can be disposed and that can deployed therefrom for the positioning and/or removal of a bone implant tip.

Additionally, an instrument of the subject invention can be configured with a slap-hammer, where a weighted collar can be slidably affixed around the elongated tube. The weighted collar can be forcibly slid along the elongated tube toward the handle or a strike-plate at or near the handle. The impact of the weighted collar against the handle or the strike-plate can act as a hammer when additional force is necessary or useful for extracting difficult or tightly compacted implant tips.

It should be noted that this Brief Summary is provided to generally introduce the reader to one or more select concepts described below in the Detailed Disclosure in a simplified form. This Summary is not intended to identify key and/or required features of the claimed subject matter. Other aspects and further scope of applicability of the present invention will also become apparent from the detailed descriptions given herein. It should be understood, however, that the detailed descriptions, while indicating preferred embodiments of the invention, are given by way of illustration only, since various changes and modifications within the spirit and scope of the invention will become apparent from such descriptions. The invention is defined by the claims below.

BRIEF DESCRIPTION OF THE DRAWINGS

In order that a more precise understanding of the above-recited invention can be obtained, a more particular description of the invention briefly described above will be rendered by reference to specific embodiments thereof that are illustrated in the appended drawings. The drawings presented herein may not be drawn to scale and any reference to dimensions in the drawings or the following description is specific to the embodiments disclosed. Any variations of these dimensions that will allow the subject invention to function for its intended purpose are considered to be within the scope of the subject invention. Thus, understanding that these drawings depict only typical embodiments of the invention and are not, therefore, to be considered as limiting in scope, the invention will be described and explained with additional specificity and detail through the use of the accompanying drawings in which:

FIGS. 2A-1 and 2A-2 illustrate an embodiment of a bone implant tip extraction instrument, according to the subject invention, that utilizes a wire grasping feature, wherein FIG. 2A-1 shows the wire retracted into the tube of the instrument and FIG. 2A-2 shows the wire being deployed from a port at the distal end of the tube and bending around the implant tip.

FIGS. 2B-1 and 2B-2 illustrate another embodiment of a bone implant tip extraction instrument, according to the subject invention, that utilizes a plurality of articulating fingers, wherein FIG. 2B-1 shows the articulating fingers retracted into the tube of the instrument and FIG. 2B-2 shows the articulating fingers deployed from the distal end of the tube so that they flare outward and away from each other over the distal end of an implant tip. Also illustrated in FIG. 2B-1 is a non-limiting example of a "slap-hammer" incorporated onto the tube.

FIGS. 2C-1 and 2C-2 illustrate yet another embodiment of a bone implant tip extraction instrument, according to the subject invention, that utilizes a web- or net-type grasping feature, where FIG. 2C-1 shows the net-type grasping feature retracted into the tube of the instrument and FIG. 2C-2 shows the net-type grasping or plug-like feature deployed from the distal end of the tube and expanded across the distal end of the implant tip to block or inhibit removal of the tube.

FIGS. 2D-1 and 2D-2 illustrate a further embodiment of a bone implant tip extraction instrument, according to the subject invention, that utilizes an adhesive-type grasping feature for adhering to a bone implant tip, where FIG. 2D-1 shows the adhesive-type grasping feature retracted into the tube of the instrument and FIG. 2D-2 shows the adhesive-type grasping feature deployed partially from ports and partially from the distal end of the tube to adhere to the interior, as well as the exterior of the implant tip for extraction.

DETAILED DESCRIPTION

Figure 1A:
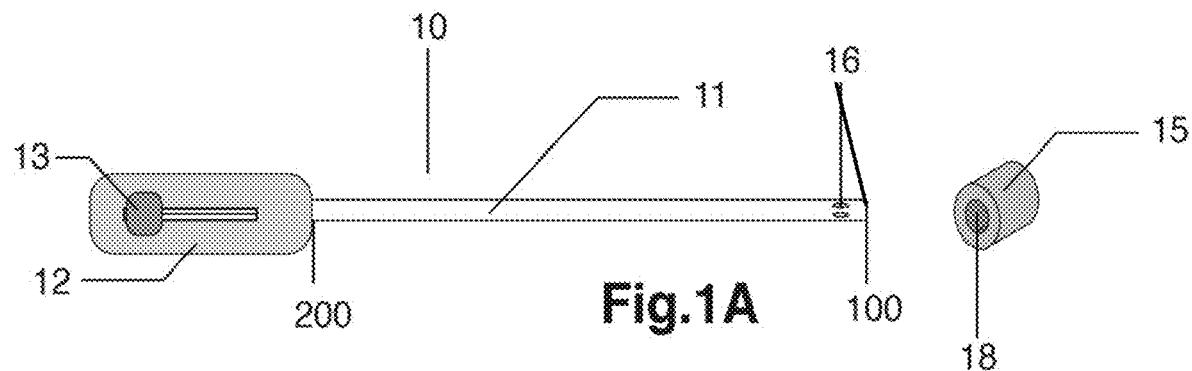
FIGS. 1A, 1B, and 1C, illustrate an embodiment of a bone implant tip extraction instrument, according to the subject invention, for positioning and removal of bone implant tips from any bone or bony structure of the body, before instrument insertion (FIG. 1A), during insertion (FIG. 1B), after instrument insertion (FIG. 1C).

The subject invention pertains to embodiments of bone implant tip extraction instruments and methods for extracting a bone tip from a bone. Embodiments can have a tubular shaft, the shaft having a distal end and a proximal end, where the surgeon can hold a handle attached to the proximal end of the shaft while inserting the opposite distal end of the shaft into a pilot hole in the bone of the patient. The system can further include a grasping feature retracted within the shaft, the grasping feature being connected to an actuator, such that the surgeon can operate the actuator to either retract or deploy the grasping feature portion, into or out of the shaft, respectively. The grasping feature is furthermore designed such that, following deployment by the surgeon, the grasping feature can be employed for the positioning and/or removal of bone implant tips of a range of potential materials and designs, including, but not limited to, bone implant tips of metal, ceramic, rigid polymer, semi-rigid polymer, elastomeric or rubber polymer, hydrogel, and composite material, or a combination of materials, formed in designs including, but not limited to, toroidal, tubular, cylindrical, prismatic, cuboid, and organic forms, with our without cannulation.

More specifically, the subject invention provides one or more embodiment(s) of bone implant tip extraction instruments or similar devices capable of being inserted into bone tissue for the removal of bone implant tips without or while minimizing undesirable incidental trauma or damage to the bone tissue of either the bone implant pilot hole, canal, or any other bone tissue near or adjacent to the bone implant tip or above-said instrument. In particular, the bone implant tip extraction instrument embodiments of the subject invention inhibit the damage or destruction of the bone tissue surrounding the bone implant pilot hole, of such bone implants as screws, nails, and other fracture fixation devices, often experienced with other known devices such as typical orthopedic surgical instruments.

The following description will disclose that the subject invention is particularly useful in the field of orthopedic surgical procedures, in particular instruments used during the surgical implantation, and/or surgical revision following implantation, of devices used for the treatment and/or repair of bone fractures. However, a person with skill in the art will be able to recognize numerous other uses that would be applicable to the devices and methods of the subject invention. While the subject application describes, and many of the terms herein relate to, a use for treatment and/or repair of bone tissue, modifications for other uses, apparent to a person with skill in the art and having benefit of the subject disclosure, are contemplated to be within the scope of the present invention.

Reference is made throughout the application to the "proximal end" and "distal end" of a bone implant tip extraction instrument. As used herein, the proximal end is that end held by or most closely to, the surgeon or operator. Conversely, the distal end is that end that moves deeper into and through interior bone tissue.

The present invention is more particularly described in the following examples that are intended to be illustrative only since numerous modifications and variations therein will be apparent to those skilled in the art. As used in the specification and in the claims, the singular for "a," "an" and "the" include plural referents unless the context clearly dictates otherwise.

Reference will be made to the attached figures on which the same reference numerals are used throughout to indicate the same or similar components. With reference to the attached Figures, which show certain embodiments of the subject invention, it can be seen that FIGS. 1A, 1B, 1C, 1D-1, 1D-2, and 1E an implant tip extraction instrument 10, according to the subject invention, which can include a shaft 11 as a hollow tube, that can be used for insertion into a bone of a patient 500, a handle 12 operably attached to the proximal end 200 and held by the surgeon or operator, an actuator 13 operably attached to the handle 12 that can be used by the surgeon or operator to retract or deploy a push rod 14 with distally located 100 grasping features 17 designed to facilitate the positioning and/or extraction of a bone implant tip 15. The shaft 11 can be formed from one or more of a variety of materials, including, but not limited to, stainless steel, titanium, and polyether ether ketone (PEEK). The push rod 14 and grasping features 17 can be formed from one or more of a variety of materials, including, but not limited to, nitinol wire or plate, stainless steel, titanium, polymer, and/or composite materials. One or more ports 16 at or near the distal end 100 of the shaft 11 can be placed in such a position as to facilitate the deployment of the actuator 14 and grasping features 17. Specific embodiments of the extraction instrument 10 are also configured with a reverse force hammer 300 (conventionally known as a "slap hammer") that includes a movable weight 310 with an aperture 312 therethrough sized for slidable engagement with the shaft 11. The moveable weight can be limited in its range of travel towards the distal end 100 of the shaft 11 by either the handle 12 or by a separate strike plate 320 connected to either the handle or to the shaft of the instrument. When the slap hammer is moved sharply towards the proximal end 50 of the shaft and collides with either the handle or the strike plate, a force is applied along the axis of the extraction instrument in the proximal direction.

The dimensions of an extraction instrument 10 can depend upon a variety of factors, including, but not limited to, the type of material being utilized for the shaft 11, the intended use in the body, the material and design of an implant tip to be extracted, and other factors that would be understood by a person with skill in the art. In a particular embodiment, the length of the shaft 11 is between the distal end 100 and the proximal end 200, is between approximately 50 mm and approximately 200 mm and the diameter is between approximately 2.5 mm and approximately 12 mm. In a more particular embodiment, the length of the shaft between the distal end 100 and the proximal end 200 is between approximately 75 mm and approximately 150 mm and the diameter is between approximately 5.0 mm and approximately 10 mm.

Figure 1B:
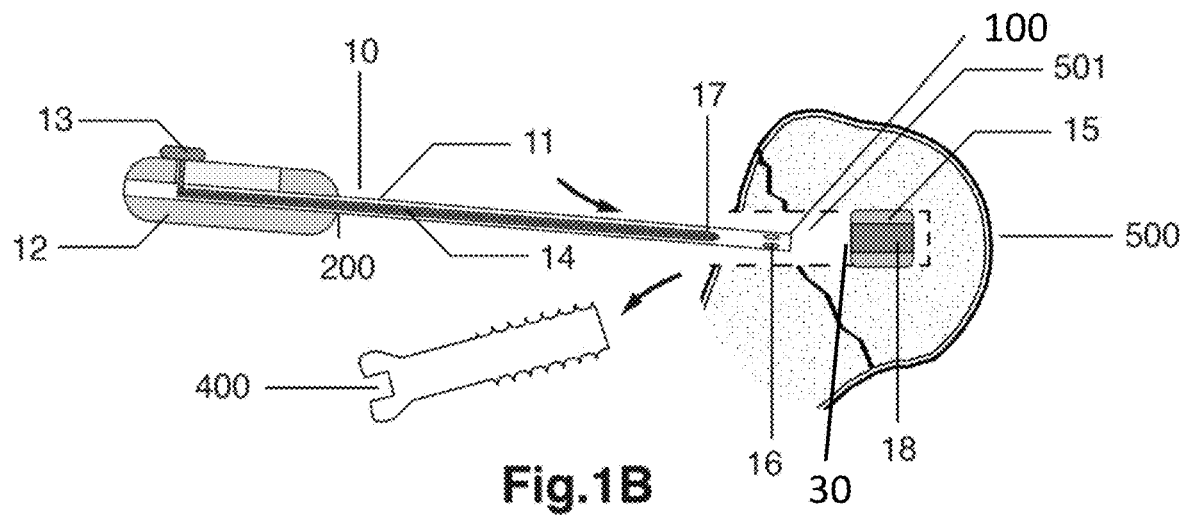
Figure 1C:
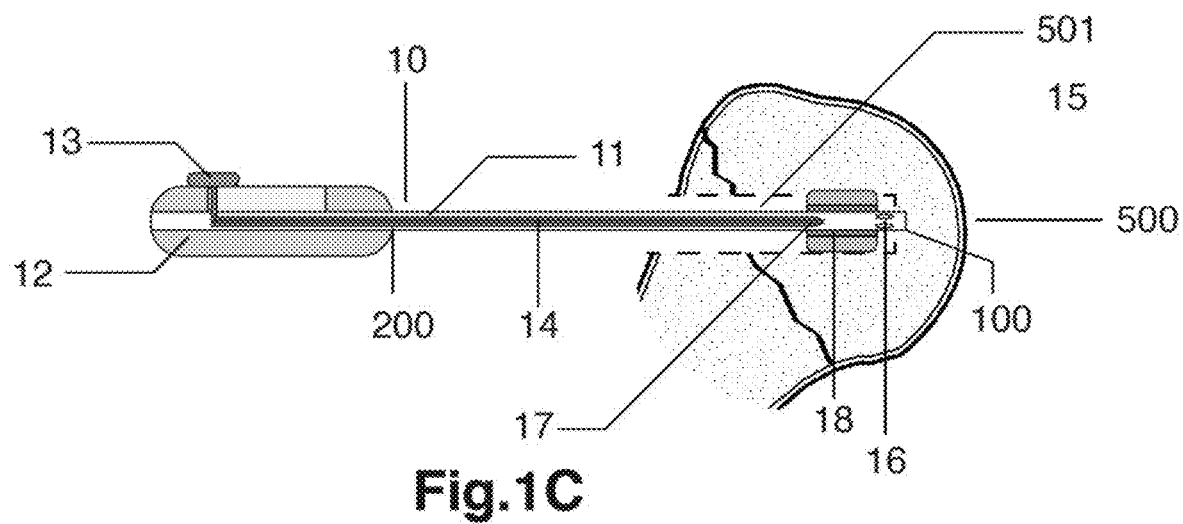

FIG. 1B shows an embodiment of a bone implant tip extraction instrument 10 during insertion into a pilot hole 501 in a bone 500, which can be performed with a bone implant 400 either present or removed from the bone pilot hole 501 or other bone cavity. FIG. 1C shows the bone implant tip extraction instrument 10 after insertion of the shaft 11 into the bone. The distal end 100 of the shaft 11 can be placed against or adjacent to the proximal end 200 of the bone implant tip 15, indicated at 30, for example, in FIG. 1B. The push rod 14 can be advanced through the bone tip, for example, through a cannulation 18 in the bone tip, so that the grasping features are deployed within or at the distal end of the bone tip. Alternatively, in the case of a cannulated bone implant tip, the shaft can extend into or through the bone implant tip cannulation 18 as shown in FIG. 1C.

Figures 1, 1D:
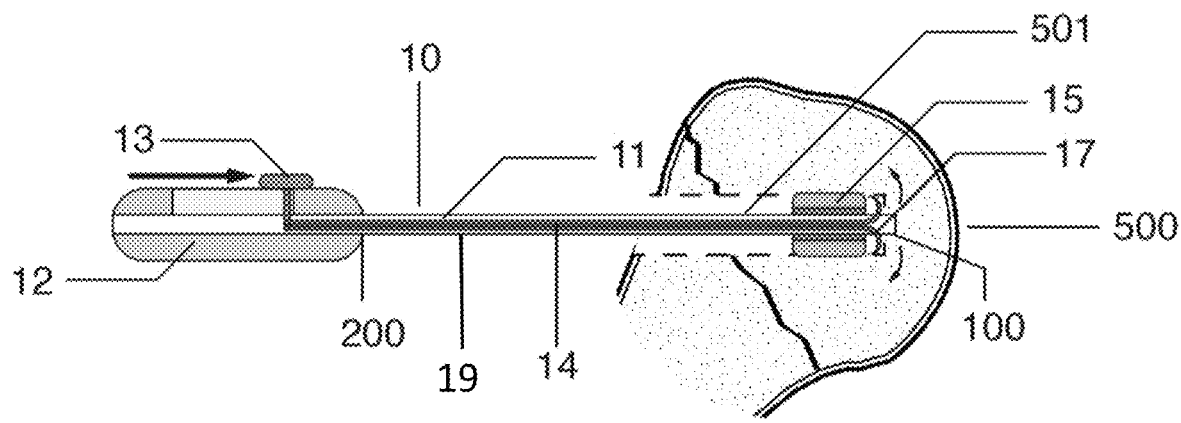
FIGS. 1D-1, 1D-2, and 1E illustrate an embodiment of a bone implant tip extraction instrument, according to the subject invention, after the distal end of the instrument has passed through an implant tip and the grasping features have been deployed from the tube of the instrument for grasping of a bone implant tip (FIG. 1D-1), being used for positioning of a bone implant tip (FIG. 1D-2), and during extraction of a bone implant tip (FIG. 1E).

FIG. 1D-1 shows an embodiment of a bone implant tip extraction instrument 10 following insertion into a bone 500, after which the surgeon or operator can use the actuator 13 to urge the push rod 14 toward the distal end 100 of the shaft 11 and/or towards a distal port 16 at the distal end of the rod or within the shaft wall 19. The push rod 14 can be formed such that, upon such advancement, the distal end of the push rod can be deployed through one or more ports 16 to form a grasping feature 17. A grasping feature can be any structure or apparatus capable of engaging with an implant tip so as to extract the implant tip through the pilot hole 501. FIGS. 1D-1, 1D-2, and 1E illustrate an embodiment having sharpened prongs that can be deployed from ports 16 in the side of the shaft 11 as shown, or, alternatively from the distal end port, which is not shown, but which would be understood by a person of skill in the art. Alternative grasping features can be, for example, a grasping hook, expandable net, actuating fingers, an adhesive, other types of apparatuses, or combinations thereof.

Figures 1, 1D, 2:
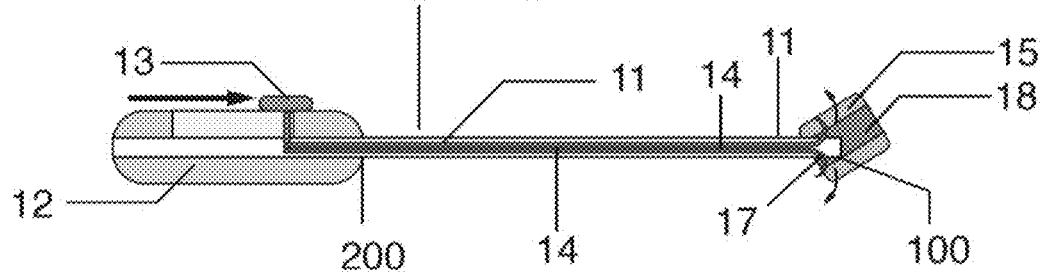
Figures 1, 2A:
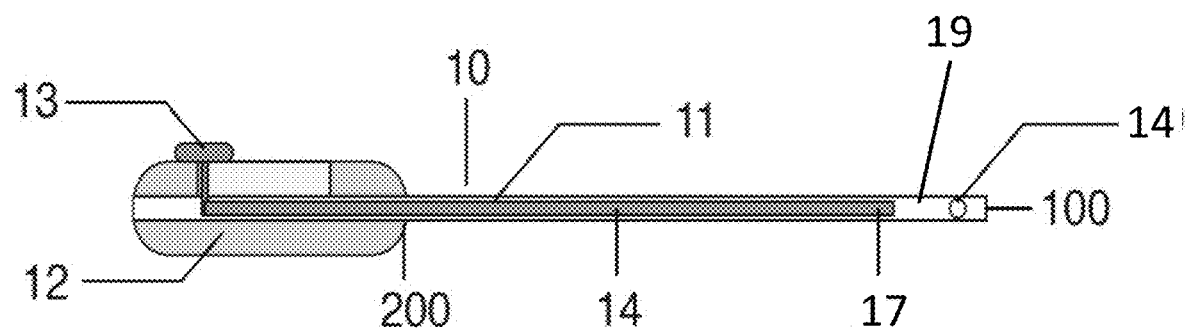
Figures 2, 2A:
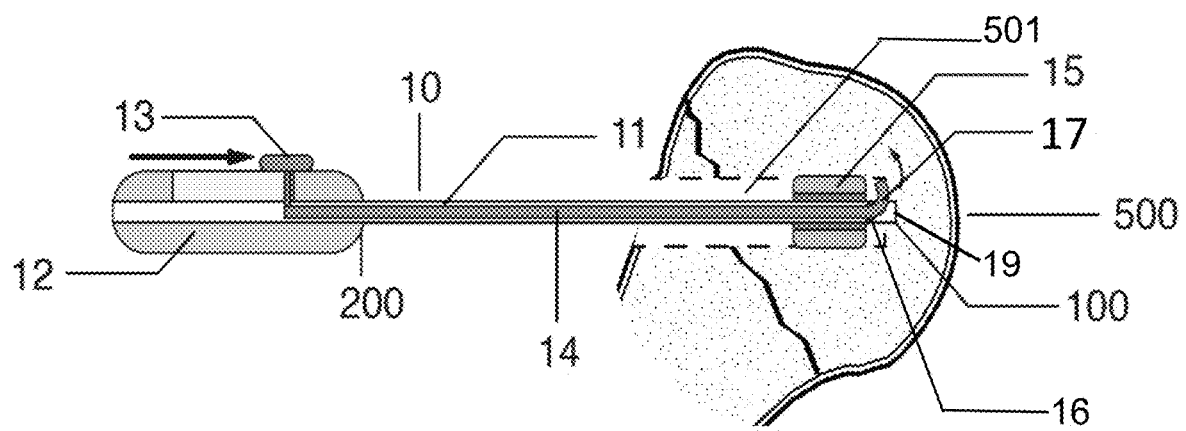

A grasping feature can be an extension of the push rod, such that the grasping feature and push rod are one unitary piece. For example, FIGS. 2A-2 shows an example of a push rod where the distal end curves into a hook to form a grasping feature when deployed from a pilot hole 16. Alternatively, the grasping feature 17 can be a separate component, such as one or more formed attachments independent of, the push rod 14. Thus, when a separate component, the grasping feature can be operably connected to the distal end of the push rod. This can allow the grasping feature to be interchangeable on the push rod. FIGS. 2C-1 and 2D-1 illustrate non-limiting examples of grasping features that are separate components from the push rod.

Figure 1E:
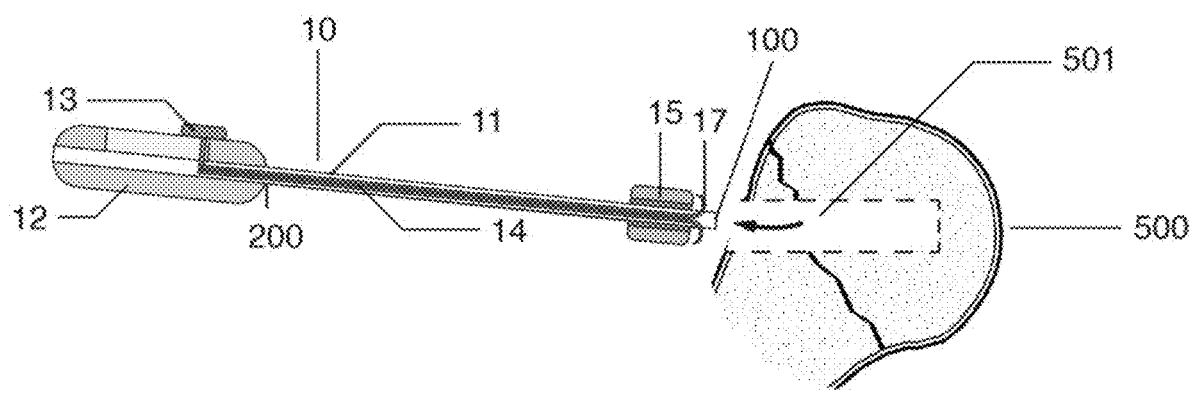

FIG. 1D-2 illustrates an alternate scenario to that depicted in FIG. 1D-1, in which the bone implant tip 15 is misaligned with the major axis of the bone implant pilot hole 501. FIG. 1D-2 shows how the grasping feature 17 of a bone implant tip extraction instrument 10 can be utilized to reposition a bone implant tip 15, if it is misaligned within the bone implant pilot hole 501 by turning or otherwise manipulating the tip to align it to facilitate extraction. FIG. 1E shows an embodiment of a bone implant tip extraction instrument 10 following removal of an implant tip 15 from a bone 500.

FIGS. 2A-1 and 2A-2 show an alternate embodiment of a bone implant tip extraction instrument 10, having a push rod 14 with an embodiment of a grasping feature 17 consisting of a grasping wire located on the distal end of the push rod 14. Following insertion into a pilot hole 501 in a bony body 500, a surgeon or operator can use the actuator 13 to urge the push rod 14 towards the distal end 100 of the shaft 11 and/or a port 16 in the shaft 11. Upon reaching either the port 16 at the distal end 100 of the shaft 11 or another port through the shaft wall 19, the grasping wire 20 design embodiment of the grasping feature 17 can be turned or bent, so as to grasp, reposition, turn, or align a bone implant tip 15 in order to facilitate extraction or extract it from a bone or bony body 500. Such a grasping wire design embodiment of the grasping feature can be formed from one or a variety of materials, including, but not limited to, nitinol wire or plate, stainless steel, titanium, polymer, and/or composite materials. Ideally, the grasping wire has a pre-configured bend or turn that is straightened at least sufficiently to be retracted into the shaft and upon deployment can automatically adopt or reassume a bent or turned configuration for engaging with or around an implant tip.

Figures 1, 2B:
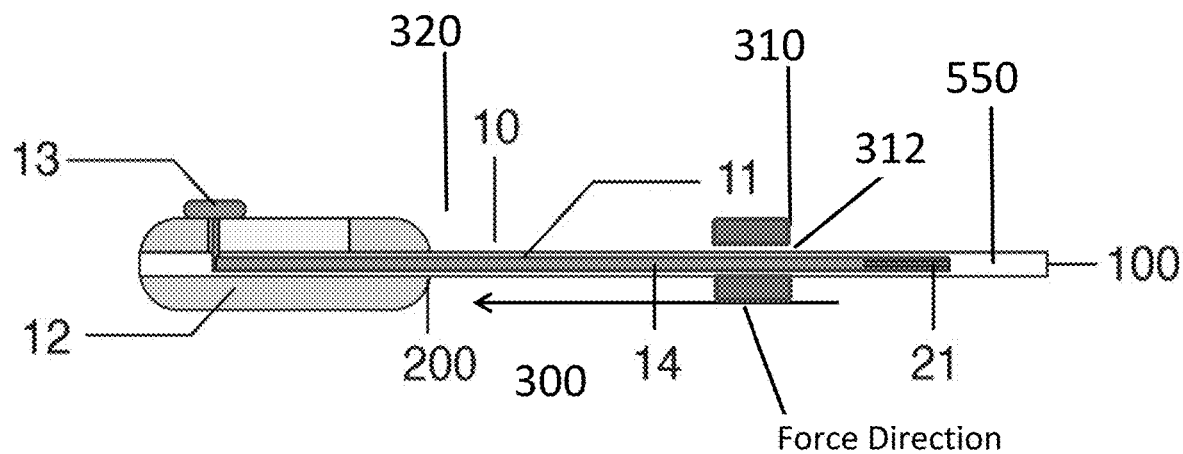
Figures 2, 2B:
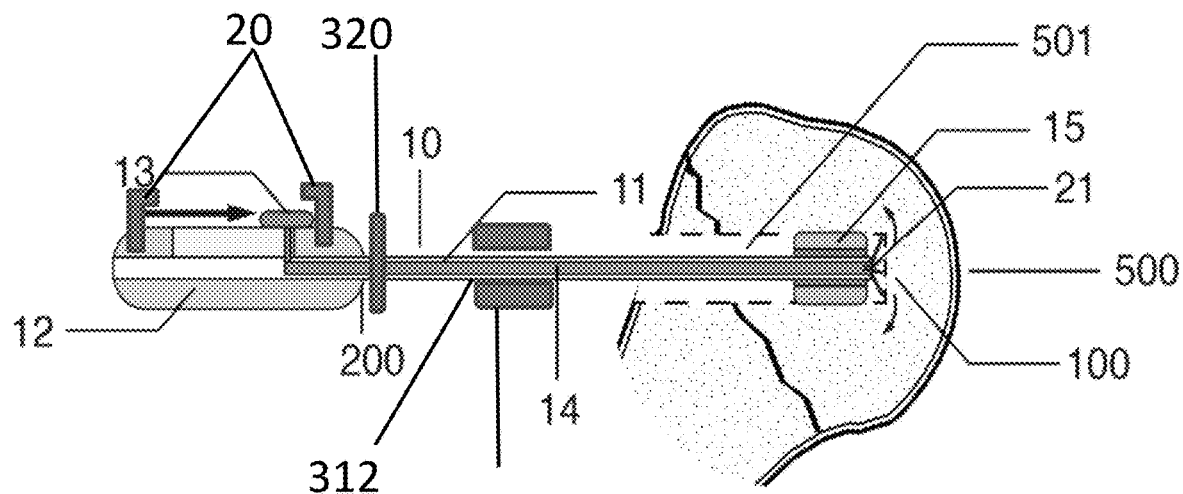
Figures 1, 2C:
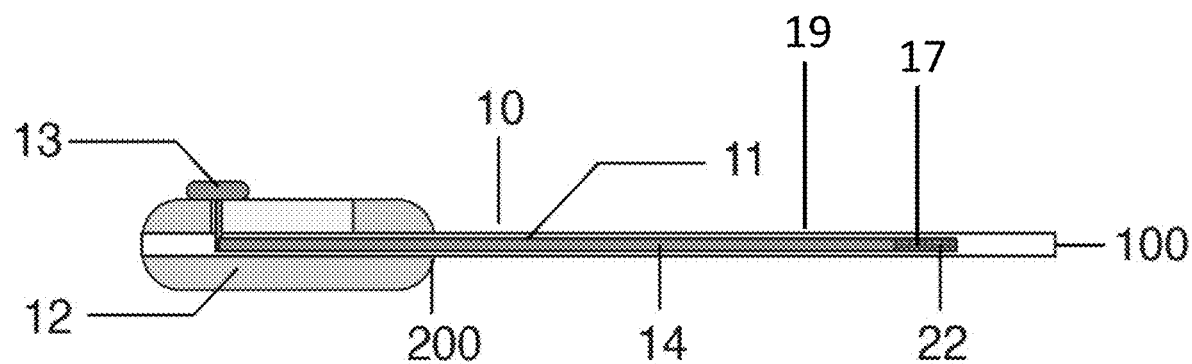
Figures 2, 2C:
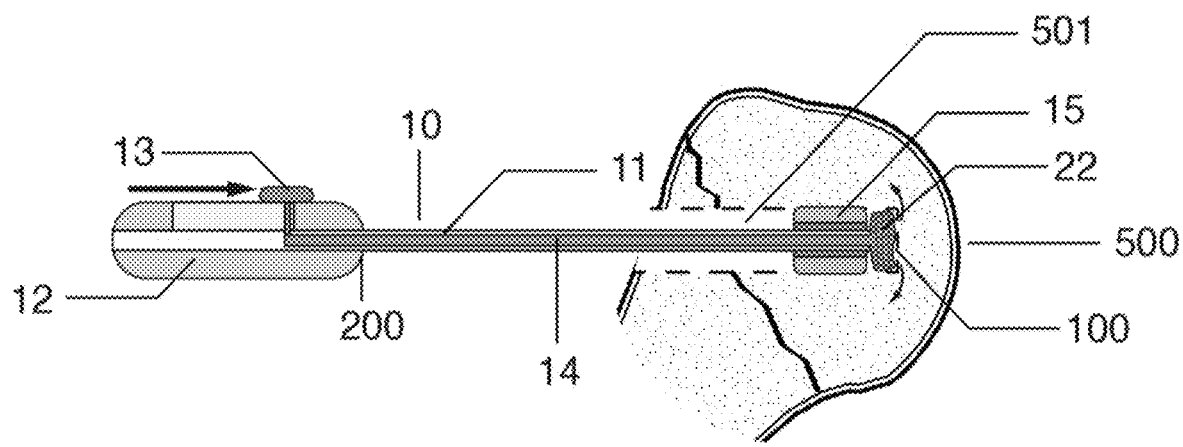
Figures 1, 2D:
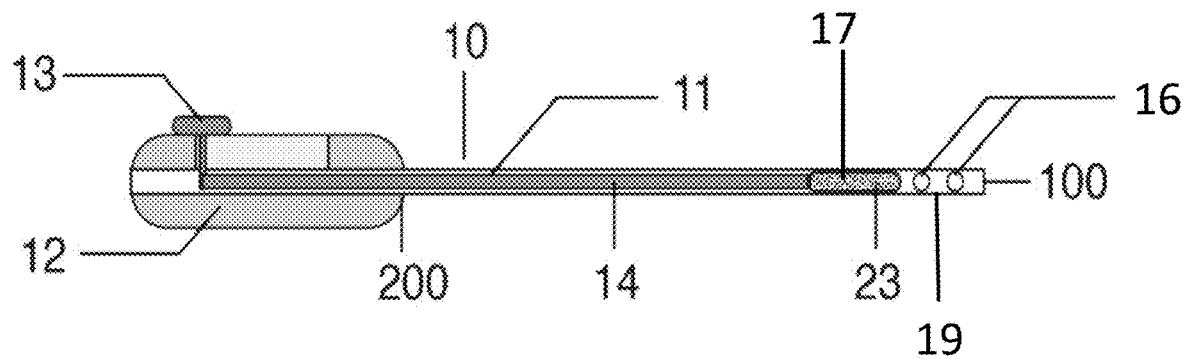
Figures 2, 2D:
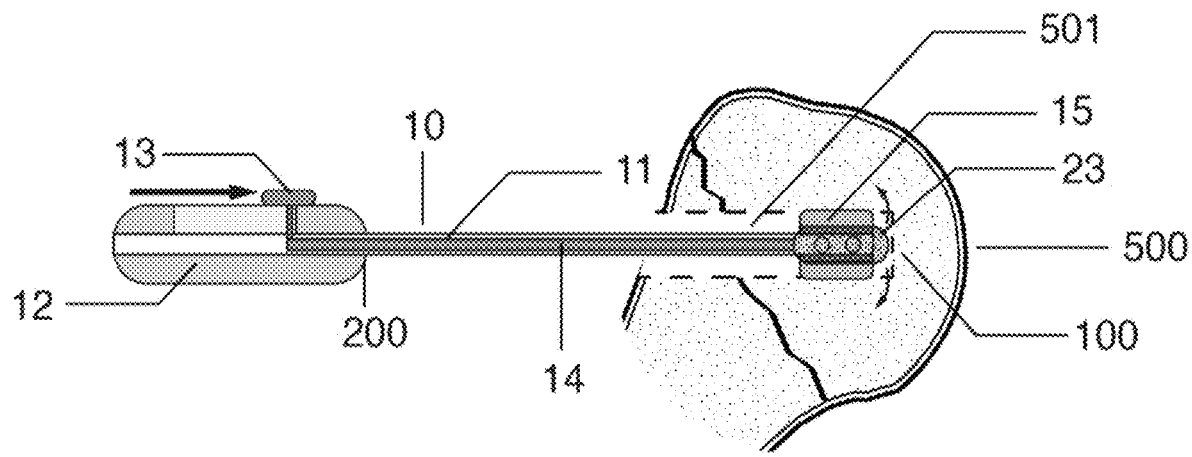

FIGS. 2B-1 and 2B-2 show an alternate embodiment of a bone implant tip extraction instrument 10, having a push rod and a grasping feature embodiment 17 consisting of a plurality of articulating fingers 21 located on the distal end of the push rod 14. Following insertion into a pilot hole 501 in a bony body 500, a surgeon or operator can use the actuator 13 to urge the push rod 14 toward the distal end 100 of the shaft portion 11. Upon reaching the port 16 at the distal end 100 of the shaft 11, the plurality of articulating fingers 21 of the grasping feature 17 can open so as to grasp, reposition, turn, or align a bone implant tip 15 in order to facilitate extraction or to extract it from a bony body 500. Ideally, the plurality of articulating fingers have a pre-configured bend or turn, such that the articulating fingers can be straightened at least sufficiently for retraction into the shaft 11, as shown, for example, in FIG. 2B-1, and upon deployment each finger can automatically adopt or reassume a bent or turned configuration for engaging with or around an implant tip. Preferably the articulating fingers flare out and away from each other, so that each points in a different direction, such as shown in FIG. 2B-2.

In some situations, an implant tip may need to be forcibly removed from a bone 500. In such situations, it can be necessary to apply force in a direction away from the grasping feature to extract an implant tip. In one embodiment, an extraction instrument 10 is configured with a reverse force hammer, sometimes referred to as a slap-hammer 300. A slap-hammer can have a moveable weight 310 with an aperture 312 therethrough and sized for slidable engagement around the shaft 11, as shown, by way of non-limiting example, in FIG. 2B-1. The moveable weight can travel towards the distal end 100 of the shaft 11. In one embodiment, the weight is stopped and force is applied to the handle 12. In an alternative embodiment, the weight is stopped and force is applied to a separate strike plate 320 connected to either the distal end 100 of the handle or to the shaft of the instrument. When the moveable weight is pushed or thrown sharply towards the proximal end 50 of the shaft and collides with either the handle or the strike plate, a force is applied along the longitudinal axis 550 of the extraction instrument, in the proximal direction.

For the slap-hammer to be effective, the grasping features must retain engagement with the implant tip 15. Otherwise, when force is applied along the longitudinal axis, the grasping features will be retracted into the shaft. In one embodiment, the handle 12 includes a locking mechanism 20 that secures the position of the actuator 13 when the grasping features are deployed. There is a variety of locking mechanisms that can be utilized with the embodiments of the subject invention. Locking mechanisms can engage with the actuator mechanism and with any other component of an extraction instrument to secure the position of the actuator, the push rod, and the grasping features after deployment. Alternatively, a locking mechanism can be further employed to secure the position of the actuator, the push rod, and the grasping features prior to deployment. A person with skill in the art will be able to determine an appropriate locking mechanism for use with an embodiment of the subject invention. Such variations are within the scope of this invention.

FIGS. 2C-1 and 2C-2 show an alternate embodiment of a bone implant tip extraction instrument 10, having a push rod 14 with an embodiment of a grasping feature 22 consisting of a net-type 22 located on the distal end of the push rod 14, such as shown, for example, in FIG. 2C-1. Following insertion into a bony body 500, a surgeon or operator can use the actuator 13 to urge the push rod 14 towards the distal end 100 of the shaft 11. Upon reaching the port 16 at the distal end 100 of the shaft 11, the net grasping feature 22 can be opened or expanded outside of the port to form a bolus, plug, or other enlarged form, such as shown in FIG. 2C-2, that inhibits the net-type grasping feature from being retracted into the shaft, so as to be used to grasp, reposition, turn, or align a bone implant tip 15 in order to facilitate extraction or to extract it from a bony body 500. Such a net-type embodiment of a grasping feature 22 can be formed from any of one or more of a variety of materials, including, but not limited to, absorbable or non-absorbable polymers.

FIGS. 2D-1 and 2D-2 show an alternate embodiment of a bone implant tip extraction instrument 10, having a push rod 14 with an embodiment of a grasping feature 17 consisting of an adhesive-type design 23 located on the distal end of the push rod 14. Following insertion into a bony body 500, a surgeon or operator can use the actuator 13 to urge the push rod 14 towards the distal end 100 of the shaft 11 and/or a port 16 at the distal end 100 of the shaft. Upon reaching a port at either the distal end 100 of the shaft 11 or one or more ports in distal end of the shaft wall 19, the adhesive-type 23 embodiment of the grasping feature 17 can be deployed to adhere to the implant tip so that the grasping feature can be turned or bent so as to grasp, reposition, turn, or align a bone implant tip 15 in order to facilitate extraction or to extract it from a bony body 500. Such an adhesive-type embodiment 23 of the grasping feature 17 can be formed from one or more of a variety of materials, including, but not limited to, bone cement, bone paste, protein-based adhesive, and absorbable or non-absorbable polymers.

The present invention, by provision of a grasping feature at the distal end of a shaft of suitable dimensions, provides advantages over the prior art device. Embodiments of the subject invention reduce the likelihood or ameliorates incidental damage to adjacent bone tissue during removal of a bone implant tip from a bony body, a problem associated with devices of the prior art. The grasping and manipulating features assist in overcoming such deficiencies by opening or expanding only after being actuated and deployed by the surgeon or operator in the vicinity of the bone implant tip to be extracted or manipulated. This permits the surgeon or operator to avoid or reduce incidental damage to the bone tissue within the bony body caused by insertion of the bone implant tip removal instrument. The grasping or manipulating features remain retracted within the shaft of the instrument, producing a smaller overall profile for the instrument during insertion, particularly insertion within a pilot hole in a bone. The grasping features provide several advantages that include:

(i) the grasping features having both an expanded and pre-expanded state, the latter occupying less volume such that the grasping features can be placed within or retracted into the shaft portion of the bone tip removal instrument;

(ii) the grasping features permitting expansion or deployment to occur under direction of surgeon or operator use of an actuator at another location along the shaft of the bone tip removal instrument, and (iii) the grasping features having the capability of grasping or manipulating a bone implant tip while causing minimal damage to adjacent bone tissue.

The scope of the invention is not limited by the specific examples and suggested procedures and uses related herein since modifications can be made within such scope from the information provided by this specification to those skilled in the art.

Any reference in this specification to "one embodiment," "an embodiment," "example embodiment," "further embodiment," "alternative embodiment," etc., is for literary convenience. The implication is that any particular feature, structure, or characteristic described in connection with such an embodiment is included in at least one embodiment of the invention. The appearance of such phrases in various places in the specification does not necessarily refer to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

We claim:

1. An extraction instrument, adapted for removing a bone implant tip from bone tissue, the extraction instrument comprising:
   a shaft comprising a proximal end and a distal end with a port;
   a push rod disposed within the shaft and comprising a proximal end and a distal end;
   an actuator operably connected to the push rod to manipulate the distal end of the push rod towards the port; and
   a grasping feature operably connected to a distal end of the push rod, the grasping feature comprising a pre-configured form that, when retracted into the shaft, assumes an at least partially straightened or pre-expanded state and that, when deployed through the port by manipulation of the actuator, resumes the pre-configured form or expanded state, to cause the grasping feature to engage with the bone implant tip.

2. An extraction instrument according to claim 1, wherein the grasping feature comprises a hook that bends or turns when deployed from the port.

3. An extraction instrument according to claim 1, wherein the grasping feature comprises a wire that bends or turns when deployed from the port.

4. An extraction instrument according to claim 1, wherein the grasping feature comprises articulating fingers that bend away from each other when deployed from the port.

5. An extraction instrument according to claim 1, wherein the grasping feature comprises a net that expands or enlarges when deployed from the port.

6. An extraction instrument according to claim 1, wherein the grasping feature comprises an adhesive that attaches to the bone implant tip when deployed from the port.

7. An extraction instrument according to claim 1, further comprising a locking mechanism for securing the position of the actuator so that the grasping feature remains deployed from the port.

8. An extraction instrument according to claim 7, further comprising a slap-hammer with a movable weight configured around the shaft and a strike plate at the proximal end of the shaft against which the moveable weight can exert force.

9. An extraction instrument according to claim 7, wherein the locking mechanism can be further utilized to secure the actuator with the grasping feature within the shaft.

10. An extraction instrument, according to claim 1, wherein the grasping feature and the push rod are a unitary piece.

11. An extraction instrument, according to claim 1, wherein the grasping feature and the push rod are formed from the same material.

12. An extraction instrument according to claim 1, wherein the grasping feature is formed from a metallic material.

13. An extraction instrument according to claim 1, wherein the grasping feature is formed from a polymer material.

14. An extraction instrument according to claim 10, wherein the grasping or manipulating portion is formed from a composite material.

15. An extraction instrument according to claim 1, wherein the shaft has a length of between approximately 50 mm and approximately 200 mm and a diameter of between approximately 2.5 mm and approximately 12 mm.

16. An extraction instrument according to claim 15, wherein the shaft has a length of between approximately 75 mm and approximately 150 mm and a diameter of approximately 5.0 mm and approximately 10 mm.

17. A method of extracting a bone implant tip from within a bone, the method comprising:
   inserting within a pilot hole in the bone the distal end of the shaft of an extraction instrument, according to claim 1, with the grasping features retracted into the shaft in the at least partially straightened or pre-expanded state;
   positioning the distal end of the shaft against a proximal end of the implant tip or extending through a cannulation in the implant tip;
   manipulating the actuator to advance the rod within the shaft, thereby causing the grasping feature to be deployed from the port in the shaft and to resume the pre-configured form or expanded state that engages with the implant tip within or around a distal end of the implant tip;
   and
   removing the distal end of the shaft from the pilot hole, while the grasping feature is engaged with the implant tip, thereby removing the implant tip from the pilot hole.

18. The method according to claim 17, wherein the extraction instrument further comprises:
   a locking mechanism for securing the position of the actuator, so that the grasping feature remains deployed from the port and engaged with the implant tip when the distal end of the shaft is removed from the pilot hole; and
   wherein the method further comprises,
   activating the locking mechanism after the grasping feature is deployed from the port and engaged with the implant tip.

* * * * *